United States Patent [19]

Burr

[11] Patent Number: 4,793,841
[45] Date of Patent: * Dec. 27, 1988

[54] PROCESS AND APPARATUS FOR FRACTIONATION OF A GASEOUS MIXTURE EMPLOYING SIDE STREAM WITHDRAWAL, SEPARATION AND RECYCLE

[75] Inventor: Peter S. Burr, Munich, Fed. Rep. of Germany

[73] Assignee: Linde Aktiengesellschaft, Wiesbaden, Fed. Rep. of Germany

[*] Notice: The portion of the term of this patent subsequent to Jul. 8, 2003 has been disclaimed.

[21] Appl. No.: 70,677

[22] Filed: Jul. 6, 1987

Related U.S. Application Data

[63] Continuation of Ser. No. 6,866,293, May 23, 1986, abandoned, which is a continuation of Ser. No. 6,610,725, May 16, 1984, Pat. No. 4,599,096.

[30] Foreign Application Priority Data

May 20, 1983 [DE] Fed. Rep. of Germany ....... 3318529

[51] Int. Cl.$^4$ ................................................ F25J 3/02
[52] U.S. Cl. .......................................... 62/27; 62/20; 62/33; 55/16; 203/98; 203/DIG. 19
[58] Field of Search .................. 62/23, 24, 27, 29, 30, 62/32, 33, 17, 20; 203/68, 70, 98, 99, DIG. 19; 55/16, 68

[56] References Cited

U.S. PATENT DOCUMENTS

| 2,690,989 | 10/1951 | Bottenberg | 62/33 |
| 3,445,347 | 5/1969 | Borrel et al. | 203/98 |
| 3,702,541 | 11/1972 | Randall et al. | 62/28 |
| 4,130,403 | 12/1978 | Cooley et al. | 55/16 |
| 4,350,511 | 9/1982 | Holmes et al. | 62/28 |
| 4,383,842 | 5/1983 | O'Brien | 62/28 |
| 4,599,096 | 7/1986 | Burr | 62/27 |

OTHER PUBLICATIONS

Technical Publication: Khimicheskaya Promyshlennost [Chemical Industry], No. 2, 1979, pp. 37–41.

Primary Examiner—David L. Lacey
Assistant Examiner—Andrew J. Anderson
Attorney, Agent, or Firm—Millen & White

[57] ABSTRACT

In fractionating a gaseous mixture, e.g. an acid gas and hydrocarbon, in a column wherein, during distillation, components of the gaseous mixture tend to form a substantially azeotropic mixture, or at least one of the components of the gaseous mixture tends to freeze out, withdrawing a side stream fluid from the column during fractionation, and separating said side stream fluid, e.g. by membranes or scrubbing, so as to remove preferentially at least a portion of one of the components of the substantially azeotropic mixture, or of the at least one of the components tending to freeze out, and recycling resultant depleted side stream to said fractionating column.

18 Claims, 4 Drawing Sheets

PROCESS AND APPARATUS FOR FRACTIONATION OF A GASEOUS MIXTURE EMPLOYING SIDE STREAM WITHDRAWAL, SEPARATION AND RECYCLE

CROSS-REFERENCE TO RELATED APPLICATIONS

This application is a continuation of application Ser. No. 06/866,293 filed May 23, 1986, now abandoned, which is a continuation of application Ser. No. 06/610,725 filed May 16, 1984, now U.S. Pat. No. 4,599,069, issued July 8, 1986.

BACKGROUND OF THE INVENTION

This invention relates to a system for the fractionation of a gaseous mixture, especially hydrocarbon mixtures, by distillation, especially at low temperatures wherein either components of the gaseous mixture form a substantially azeotropic mixture or at least one of the components of the gaseous mixture tends to freeze out.

By way of definition, the term "distillation" used herein is intended to embrace rectification as well as other conventional distillation processes. The term "substantially azeotropic mixture" is intended to embrace true azeotropic as well as approximate azeotropic mixtures, e.g., equilibrium mixtures of $CO_2$ with $H_2S$ which at certain constant pressures exhibit $CO_2$ concentrations in the vapor phase that are everywhere greater than those in the liquid phase, but where the concentrations of $CO_2$ in the vapor and liquid phases are nearly identical over an extended composition range.

Fractionation processes pertinent to this invention have been described in "Hydrocarbon Processing", May 1982, pp. 131-136. If a gaseous mixture is to be fractionated wherein the components during distillation form a substantially azeotropic mixture, then product purity is limited by the concentration of the components at the azeotropic point. In the distillation of other gaseous mixtures at low temperatures, where the reflux liquid is insufficient to maintain all of the components in solution at the cold temperatures, one or more of these components begin to freeze out, thereby terminating the distillation.

One suggested solution to the problem proposed in the aforementioned prior publication resides in admixing to the reflux liquid in the column an additional component, such as n-butane or a mixture of light or heavy hydrocarbons. Such admixture has the effects of increasing the amount of reflux liquid, altering the composition of the liquid, and increasing the temperature in the column. These effects, in the one case, suppress the deposition of solids which would otherwise freeze out, and in the other case with azeotropic mixtures results in an improvement of the purity of the fractionation products. The added components are then withdrawn from the distillation column and recovered in a supplemental distillation stage.

This suggested process, however, has several disadvantages. For example, in the separation of the addition component in the downstream supplemental distillation stage another azeotropic mixture occurs in part, for example ethane and carbon dioxide. Consequently, an additional component must also be introduced into this supplemental downstream distillation stage and this increases the cost of the process.

A further disadvantage resides in that the additionally introduced component causes dilution of the reflux liquid in the column, thus increasing the work of separation in the column. Still another disadvantage is that the additional component that must be fed to the column as a cold liquid is heated, during its downward flow within the to the higher temperature of the liquid in the column p, so that a large portion of the cold value is dissipated.

SUMMARY

An object of one aspect of this invention is to provide one or more processes of the type mentioned hereinabove but which exhibit improved economics for the separation of gaseous mixtures containing components tending to freeze out or for substantially azeotropic mixtures.

According to an object of another aspect of this invention, apparatus is provided for conducting such improved processes.

Upon further study of the specification and appended claims, further objects and advantages of this invention will become apparent to those skilled in the art.

Though the process of this invention is applicable to gaseous mixtures containing substantially azeotropic mixtures or components which tend to freeze out, it is to be understood that the two types of gaseous mixtures exhibit different problems, and that in the absence of this invention, there would be no suggestion that the invention disclosed herein could be used for both types of mixtures.

To attain the objects of this invention, a system is provided wherein during distillation, at least a partial stream containing components of the substantially azeotropic mixtures, and/or of the component(s) tending to freeze out, is removed from the column, subjected to separating to deplete the removed distillation medium in a component of said substantially azeotropic mixture or in said component(s) tending to freeze out, and resultant depleted distillation medium is recycled to the distillation column.

In the process of this invention, a vapor-phase or liquid fluid is withdrawn from the fractionating column, preferably as a side stream, e.g., from a plate above the bottom plate and below the top plate, the composition of the fluid is changed, and then the resultant altered fluid returned into the column in the vapor of liquid phase. In direct contrast to the previously known process, altering of the composition takes place by separating specific components from the fluid to be returned to the column, rather than by adding an additional component.

It is possible by the process of this invention to fractionate gaseous mixtures tending to form azeotropic mixtures or tending to produce solid deposits in the fractionating column. This eliminates the difficulties inherent in the prior art method of introducing an additional component. Distillation in this invention is thus improved by separating part of the gaseous components. ponents.

In particular, when a component which tends to freeze out is removed, not only is there an advantage because of the reduction in the concentration of this component in the column, resulting from the increased reflux liquid from the recycled stream, but there is also an advantage because the effective amount of this component is reduced, which reduces the work required for separating this component in the column. This compensates for the work required to separate the component in the supplementary separation process.

In an advantageous further aspect of the process of this invention, the fluid to be returned is withdrawn at certain levels, e.g., in a column of 20 theoretical plates, the fluid is withdrawn at anywhere from the 2nd to the 19th plate, and especially at the middle in the case of approximate azeotropic mixtures, whereas in the case of freezing of components it is withdrawn from about the 10th to the 19th plates, especially at approximately the middle or upper third of the column.

The recycle of the fluid admittedly entails a certain dilution of the process streams in the column, but this dilution is restricted to a limited zone of the column, whereas in the conventional introduction of an additional component, the entire column, down to the sump, is traversed by a stream of dilute reflux liquid. The cold values contained in the withdrawn fluid can be utilized oor cooling the gaseous mixture to be fractionated or, in conjunction with a heat pump, for cooling the head of the column. Therefore, the process as conducted according to this invention not only prevents freezing out, but also improves the economics of the distillation step.

In a preferred embodiment of another aspect of the process of this invention, separation of the withdrawn distillation medium is conducted by a physical or chemical scrubbing step.

In another advantageous aspect of the process of this invention, the separation is conducted by diffusion on semipermeable membranes.

Because of their substantially different diffusion characteristics, acid gases, such as $H_2S$ or $CO_2$, can be separated by diffusional processes from methane, ethane and/or higher paraffins. The use of semipermeable membranes for this purpose is highly economical with respect to both apparatus costs and energy consumption. Such semipermeable membranes are conventional and include, but are not limited to: cellulose acetate, polysulfanone, silicone rubbers, polyesters. Cellulose acetate is preferred for the separation of $CO_2$ and $C_2H_6$, but the choice of membrane will depend on the actual components to be separated, and the operating conditions of the membrane, and other equipment.

For further details on the separation of gases by membrane permeation, reference is made, for example, to Perry and Chilton, Chemical Engineer's Handbook, 5th Edition, 1973, McGraw-Hill, pp. 17-34 through 17-38.

In a preferred further aspect of the process of this invention, the gaseous mixture to be fractionated contains an acid gas and a hydrocarbon. Suitable acid gases include, but are not limited to, $CO_2$ and $H_2S$; suitable gaseous hydrocarbons include, but are not limited to, methane, ethane, and propane. Examples of gaseous mixtures to be fractionated in percent by volume are: (A) $CH_4$ (about 5 to 20%), $CO_2$ (about 50 to 90%) and $C_2H_6$ (about 2 to 20%); and (B) Chd $4H_{10}$ (about 10 to 50%), $C_3H_8$ (about 10 to 50%), $H_2S$ (about 10 to 50%) and $C_2H_6$ (about 10 to 50%). (A) is a mixture containing components which tend to freeze out, and (B) is a mixture containing substantially azeotropic mixtures.

Advantageously, the gaseous mixture contains an acid gas as well as two other components having different boiling poits, and in particular, the distillation medium to be recycled is withdrawn from the column at the zone of the highest concentration of the component having the intermediate boiling point.

If the mixture contains, for example, an acid gas, as well as methane and ethane as the other components, then the medium to be recirculated is withdrawn from the column at the zone of the highest ethane concentration in the latter. Since ethane is capable of dissolving the large amounts of acid gas, and moreover increases the temperatures at the column plates, this aspect of the invention is of special advantage for the fractionation. Although a maximum in the ethane concentration would occur in the column even without the separation of the component tending to freeze out, the separation steep of this invention substantially enhances this effect. Thus, it would be necessary to determine the location in a column of the maximum ethane concentration and at substantially that location, withdraw the side stream from the distillation medium.

The formation of a high ethane concentration is especially beneficial if, in a further aspect of the process of this invention, the depleted distillation medium is returned into the column above the point of withdrawal.

A high ethane concentration not only prevents freezing and of acid gas, but also additionally increases the amount of reflux in the column and moreover increases the efficiency of the diffusion process — if semipermeable membranes are used for separation purposes. The reason for this increased efficiency is that the relative permeability of, for example, cellulose acetate membranes for, e.g., $CO_2/CH_4$-mixtures is about ten times as low as for $CO_2/C_2H_6$-mixtures. As a consequence, the acid gas can be separated from the withdrawn dsstillation medium without a large loss of ethane. By using the operating procedure of the process described with reference to the hereinafter described example of separating an acid gas-methane-ethane mixture, the largest part of the methane can also be recovered.

Since ethane has a higher concentration in the liquid then in the vapor phase, the distillation medium to be recycled is suitably withdrawn from the column in the liquid phase. Inasmuch as liquid ethane is a good solvent for the acid gas component tending to freeze out, the acid-gas-depleted distillation medium is also suitably returned into the column in the liquid phase.

In the fractionation of gaseous mixtures tending to form azeotropic mixtures, it may be advantageous under certain circumstances to return the fluid to be recycled at below the point of withdrawal into the column The exact positions where the fluid should be removed and returned to the column depend upon the compositional profiles in the column and upon the influence of compositional changes on the phase equilibria of the fluids within the column, and upon the specifications for the products of the column and supplementary separating process. The recycling of the depleted stream to a point below the point of removal would normally be required in the case of an approximate azeotropic mixture occurring in the lower part of the column, said mixturing being such that an improvement in separation may be achieved by addition of a component present in the upper part of the column.

Recycling of the depleted stream to a position above the point of removal would normally be required in the case of either the freezing of one or more components or in the case of an approximate azeotropic mixture occurring in the upper part of the column, said mixture being such that an improvement in separation may be obtained by addition of a component present in the lower part of the column.

In an advantageous further aspect of the process of this invention, the acid gas component of the distillation medium recycled into the column is at most 5 and preferably no more than 3 mol% of the recycled medium.

The acid gas proportion may, in any case, only be of such a magnitude that no solids are precipitated during recycling into the column.

If the fluid withdrawn from the column is conducted over semipermeable membranes, it must be compressed beforehand so as to at least compensate for the resultant pressure loss. Compression also simultaneously contributes to part of the refrigeration required in the process. As a result of the increased pressure ratio the separation of the components can be made sharper. A high ethane concentration also contributes to a sharp separation because the rate of permeation of ethane is very low compared to the acid gases, e.g., $CO_2$. Alternatively, for a constant pressure ratio, the pressure on the low pressure side of the membrane may be increased. A superatmospheric pressure is desirable to prevent ingress of air which could produce explosive mixtures with any hydrocarbons contained in the permeate stream; it also obviates the need for an expensive and energy intensive vacuum pump.

In a further embodiment of the process of this invention, the gaseous stream diffusing through the semipermeable membranes, which stream contains essentially acid gas, e.g., $CO_2$, is mixed with the sump product of the column also rich in $CO_2$. These $CO_2$ streams are reused, for example, in tertiary oil recovery. Details of a tertiary oil recovery process employing $CO_2$ or the like are found in the literature, e.g., B. C. Price, F. L. Gregg "$CO_2$/EOR: from source to resource" 62nd Annual GPA Convention Mar. 14-16 1983, San Francisco, published also in Oil & Gas Journal, Aug. 22, 1983.

In a preferred further development of the process of this invention, the gaseous mixture to be fractionated comprises natural gas or a gaseous petroleum component, e.g., propane. This invention is especially applicable to the distillation of a gaseous mixture which is a gas recovered from a tertiary oil recovery process, wherein $CO_2$ is injected as the motive gas into a well hole for expelling and reducing the viscosity of oil as discussed above. Thus, (a) the feed gas into the well hole and (b) the withdrawn gas from the formation respectively comprises: (a) the separated $CO_2$ fraction and (b) the feed gas associated with the distillation process of this invention.

DETAILED DESCRIPTION

Figure 1:
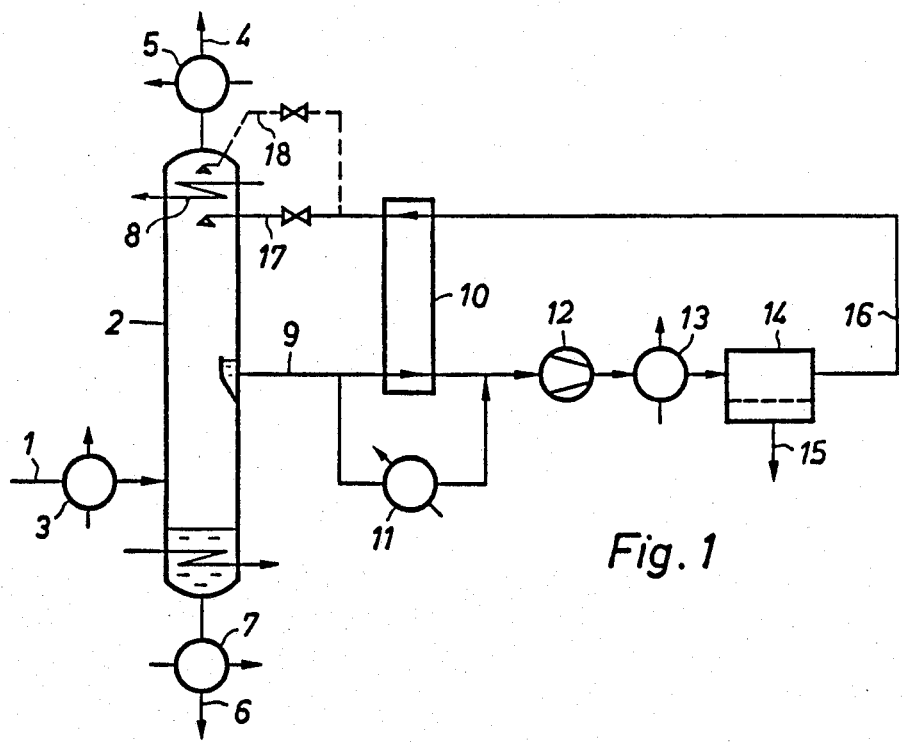
FIG. 1, 2 and 5 are schematic flowsheets showing three different preferred embodiments of the process of this invention and the apparatus associated therewith.

In the process illustrated in FIG. 1, there is introduced into column 2 there is introduced via conduit 1 a gaseous mixture having the following characteristics:
 composition (by volume): 50% $CO_2$, 45% $CH_4$, 3% $C_2H_6$, 2% $C_3$ hydrocarbons;
 pressure: about 36 bar;
 temperature: about 300 K;
 throughout rate: 100 mol/sec.

After being cooled to about 230 K in a heat exchanger 3, the gaseous mixture is introduced into column 2, operated under a pressure of about 35 bar, and is fractionated therein into a methane-rich, gaseous fraction 4, removed at the head of column 2, as well as into a liquid fraction 6 rich in carbon dioxide, withdrawn at the bottom of column 2. Fractions 4 and 6 are heated in heat exchangers 5 and 7 respectively to about 300 K.

The methane-rich fraction 4 contains at most 2% $CO_2$; the withdrawn quantity is about 43 mol/sec. The $CO_2$-rich fraction 6 contains about 87% $CO_2$, the withdrawn quantity is about 43 mol/sec. The pressure of the two fractions 4 and 6 is respectively about 34 bar.

The temperatures in column 2 range between about 180 K (head) and about 260 K (bottom). In the zone containing the head condenser 8, (approximately in the upper third of column 2) a portion of the $CO_2$ would ordinarily be precipitated in solid form owing to the conditions present at that location.

In order to avoid such precipitation, a liquid stream 9 is withdrawn from column 2 approximately at the level of the middle of the column, the characteristics of this stream being 42% $CO_2$, 21% $C_2H_6$, 37% $CH_4$, 25 mol/sec. This stream 9 is divided into two partial streams which are heated and vaporized in heat exchanger 10 and/or heat exchanger 11 and are subsequently recombined. The stream 9 is then compressed in a compressor 12 to about 50 bar and, after removal of the heat of compression in a cooler 13, introduced at about 300 K into a membrane separation unit 14 provided with semipermeable membranes. Based on the differential permeabilities of the membranes for the various gaseous components, a fraction 14 with about 73% $CO_2$ (14 mol/sec with about 1.5 bar) is removed on the low-pressure side of the separator 14, whereas a fraction 16 depleted in $CO_2$ (about 3% $CO_2$, 45% $C_2H_6$, 52% $CH_4$, 11 mol/sec) is obtained on the high pressure side of the separator The semipermeable membrane is e.g., cellulose acetate.

After the predominant part of the $CO_2$ has thus been separated, the remaining gas is cooled in heat exchanger 10, expanded, and thereby at least partially liquefied, and finally returned into column 2 below (conduit 17) or about (dashed-line conduit 18) of the head condenser 8. If desirable, the stream 16 can also be recycled in an entirely gaseous condition to the column. This could be advantageous with respect to the construction of the heat exchangers 10, 33 or 8 inasmuch as it might be advantageous to condense the recycled stream in the condenser of the column rather than in an external exchanger. This depends on a number of factors such as heat loads, enthalpy-temperature diagrams, gas-liquid velocities, construction limits, etc. It might also be advantageous with respect to distribution of the recycled $C_2H_6$ within the column or cooling coils.

Furthermore, if desired, the $CO_2$-rich fraction 15, after compression, can be mixed with the $CO_2$-rich fraction 6 from column 2. In this way, a larger quantity of $CO_2$ can be passed, for example, to a tertiary oil recovery system and the gas recovered therefrom can after dehydratio and other necessary preprocessing be treated as feed gas in conduit 1.

In the same apparatus operating in analogous manner, it is also possible to rectify a gaseous mixture which, during fractionation in column 2, would otherwise form a substantially azeotropic mixture. Examples of such a mixture include but are not limited to mixtures of $CO_2$ with $C_2H_6$ and other hydrocarbons, and $H_2S$ with $C_2H_6$ and other hydrocarbons.

Figure 2:
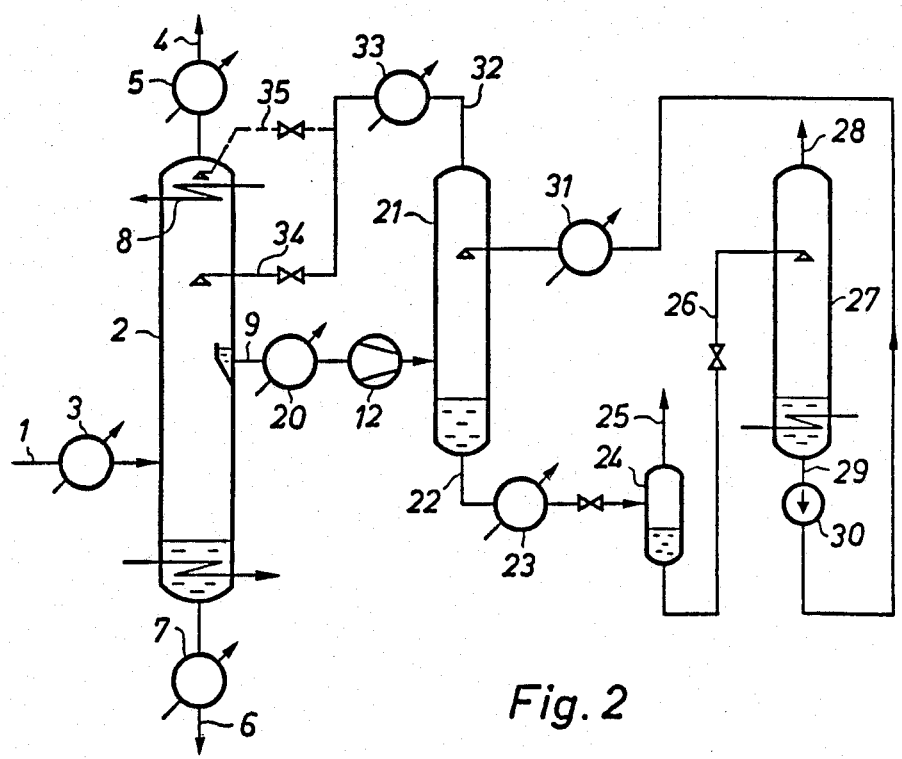

FIG. 2 illustrates a system similar to that of FIG. 1, but with the difference being that separation of $CO_2$ from the liquid stream 9 withdrawn from column 2 takes place by scrubbing rather than by membrane separation. (Corresponding structural components bear reference numerals identical to those in FIG. 1.)

The liquid stream 9 taken from column 2 is heated and vaporized in heat exchanger 20 and subsequently compressed in compressor 12. As an alternative to compressor 12, it is also possible to provide a liquid pump upstream of heat exchanger 20.

In order to separate the $CO_2$, the compressed gas is fed to a scrubbing column 21 where the $CO_2$ is absorbed by a chemical or physical scrubbing medium. Examples of a physical scrubbing agent include, but are not limited to, N-methyl-2-pyrrolidone, and for a chemical scrubbing medium, methyldiethanolamine. The preferred scrubbing medium is methyldiethanolamine in water.

A gas extensively free of $CO_2$ is removed in conduit 32 from the heat of the scrubbing column 21; after being cooled in cooler 33, this gas is expanded and reintroduced into column 2 either via conduit 34 below the head condenser 8 or via the conduit 35, illustrated in dashed lines, above the head condenser 8. Recycling takes place, depending upon requirements, in the gaseous or liquid condition. Depending on the scrubbing medium used and column temperatures it may be necessary to remove traces of the scrubbing medium from the stream 32 before returning it to the column in order to prevent precipitation of solid phases in the heat exchanger 33, valves 34 or 35 or column 2. In the case of methyldiethanolamine dissolved in water, a solid absorbent may be used.

At the bottom of the scrubbing column 21, a liquid 22 is removed containing essentially $CO_2$ and the scrubbing medium. The liquid is heated in a heat exchanger 23, expanded, and fed to a phase separator 24 where a $CO_2$-rich fraction 25 is withdrawn overhead. The liquid fraction 26 from phase separator 24 is expanded and introduced into a column 27 wherein extensive fractionation takes place into a gaseous overhead fraction rich in $CO_2$ withdrawn via conduit 28 and into a liquid fraction essentially containing regenerated scrubbing medium and withdrawn via conduit 29. The scrubbing medium in 29 is returned into scrubbing column 21 by means of a pump 30, but prior to recycling, cooling of the scrubbing medium is effected in a heat exchanger 31.

Figure 3:
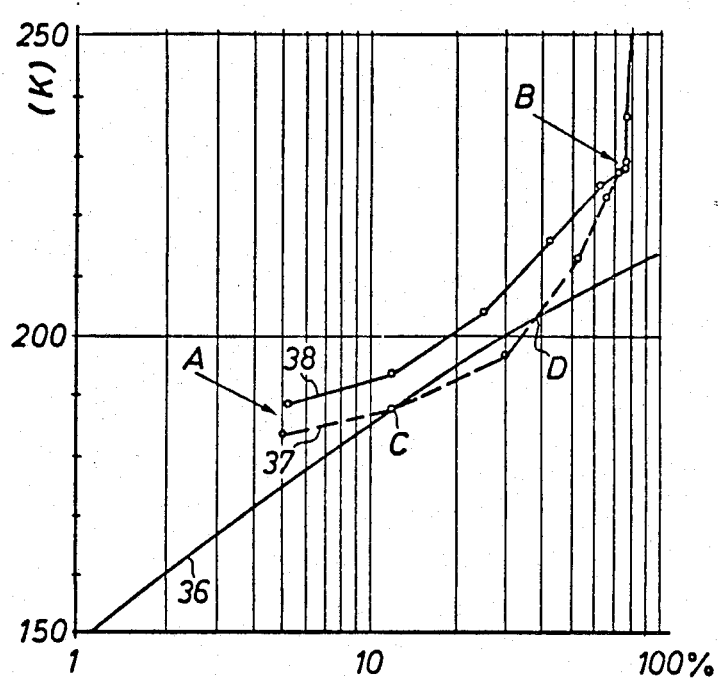
FIG. 3 is a solubility diagram of $CO_2$ in liquid in various zones of a distillation column.

FIG. 3 is a diagram of the solubility of $CO_2$ in the interior of column 2, the ordinate being the temperature plotted in Kelvin and the abscissa being the $CO_2$ proportion in the liquid, in percent. The curve 36 describes the solubility limit of $CO_2$, below which $CO_2$ precipitates in the solid phase. Curves 37 and 38 indicate the $CO_2$ concentration in the liquid on the column plates, namely for the zone between the head of the column (A) and the point of introduction of the feed stream 1 (B). The dashed-line curve 37 shows the course of distillation without removal, and curve 38 demonstrates the course with the removal of liquid at 9, and recycling of said liquid after separation of a large part of the $CO_2$. It can be seen from this illustration that, without utilizing the present invention, $CO_2$ would be deposited in solid form between points C and D, by operating according to this invention, the $CO_2$ remains clearly above the solubility limit thereby avoiding the deposition of solids.

Figure 4:
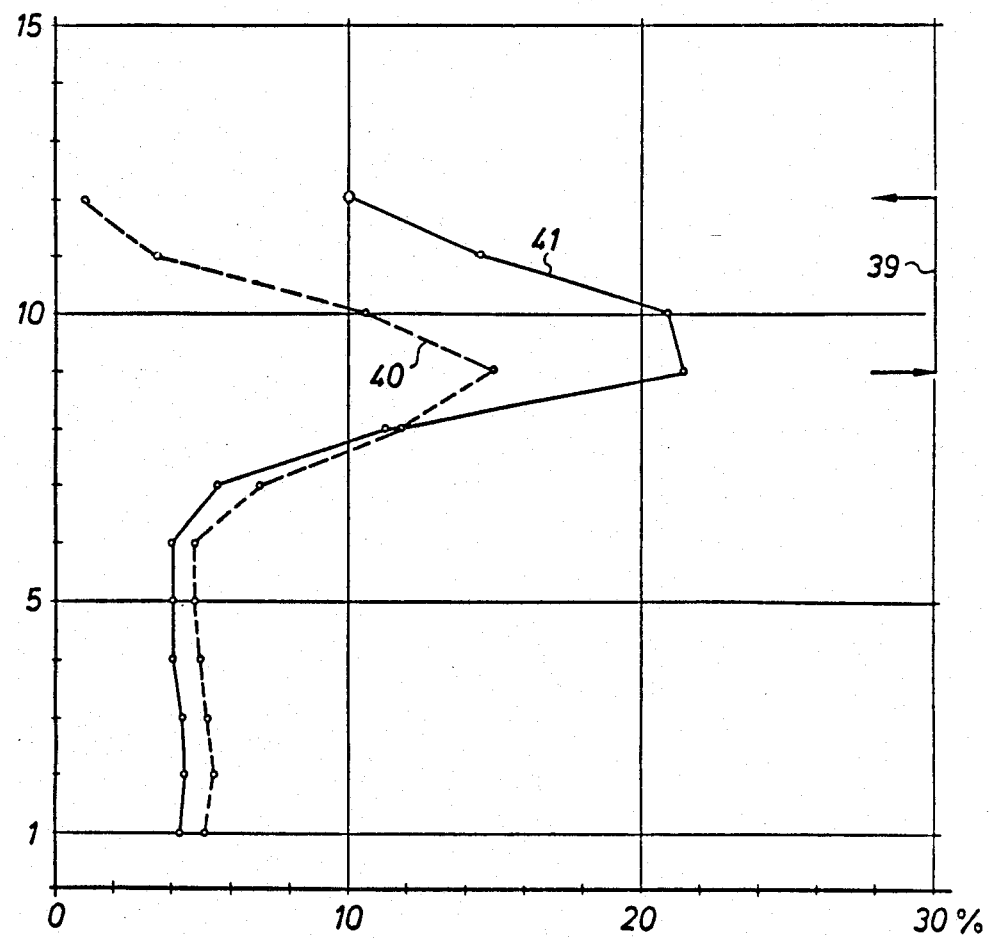
FIG. 4 is a $C_2H_6$ concentration diagram.

FIG. 4 is a graph of the concentration of $C_2H_6$ in column 2 having a total of 12 theoretical plates. The number, starting from the bottom of the column, of the theoretical plates is plotted as the ordinate against the $C_2H_6$ concentration of the liquid in molar percent as the abscissa. The arrow 39 symbolically represents the withdrawal of liquid via conduit 9 on the 9th theoretical plate and return thereof via conduit 17 or 34 on the 12th theoretical plate, respectively. Without such recirculation, the curve 40 in dashed lines represents the $C_2H_6$ concentration, whereas solid curve 41 is obtained using the recirculation mode of this invention. It can be seen that the liquid to be recycled is withdrawn at the point of highest ethane concentration, and that the ethane concentration in the region of maximum concentration clearly increases by utilizing the process of this invention. Since $CO_2$ is highly soluble in liquid ethane, the increased ethane concentration is a further factor in preventing $CO_2$ precipitation.

Figure 5:
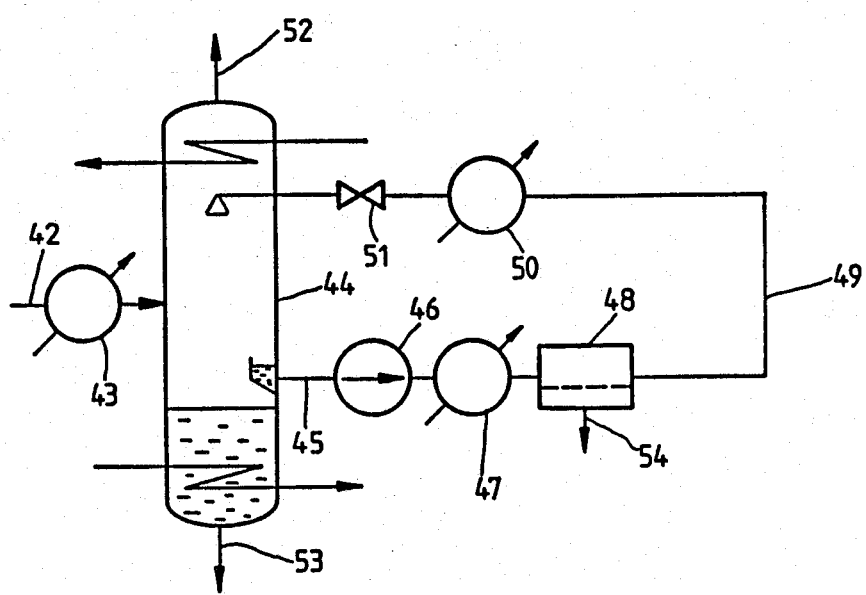

FIG. 5 shows an example for the separation of a mixture containing an approximate azeotropic mixture. A mixture 42 of e.g. 40% $C_2H_6$, 40% $H_2S$ and 20% n $C_4H_{10}$ is cooled in a cooler 43 and fed to a distillation column 44. In the column 44, $H_2S$ and $C_2H_6$ tend to form an azeotropic mixture, if the concentration of $C_2H_6$ is near 100%.

A liquid side stream 45 is withdrawn from below the middle of column 44, is pumped by a pump 46 through an evaporator 47 into a membrane separation unit 48. A fraction 54 enriched in $H_2S$ is removed on the low-pressure side of the separator 48, whereas a fraction 49 depleted in $H_2S$ is obtained on the high pressure side of the membrane. This fraction containing a high concentration in $C_4H_{10}$ is cooled and liquified in a cooler 50, expanded in valve 51, and recycled into column 44 above the point of withdrawal. By this, the concentration of $C_4H_{10}$ in tee column will be increased with the result that the $C_2H_6/H_2S$ - azeotrope in the upper part of the column can be broken. $C_2H_6$ is withdrawn via line 52 from the head of column 44, a liquid mixture of n $C_4H_{10}$ with $H_2S$ is withdrawn from the sump of column 44 by line 53.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages an conditions.

I claim:

1. A process for fractionating a gaseous mixture by distillation in a fractionating column wherein, during distillation, at least one of the components of the gaseous mixture is present in the fractionating column in a sufficient concentration to freeze out in a non-hydrated form as a solid under distillation conditions in the column in the absence of a preventive step and another one of the components is present in the fractionating column in liquid phase, said another one of the components having the highest dissolving capacity of the freezable component, said process comprising withdrawing a sidestream fluid form the column during the fractionation at a point in the column where: (a) the freezable component is at a concentration lower than the maximum concentration and (b) where the high dissolving component is at substantially the maximum concentration, and separating said fluid so as to remove preferentially the at least one of the components and recycling resulted depleted stream to said frationating column, said depleted stream having a higher dissolving capacity for the at least one of the components than the stream withdrawn.

2. A process according to claim 1, wherein said sidestream fluid is withdrawn, height-wise, from approximately the middle or upper third of the column.

3. A process according to claim 1, wherein said separating of said sidestream is conducted by a physical or chemical scrubbing step.

4. A process according to claim 1, wherein said separating of said side fluid is conducted by diffusion on semipermeable membranes.

5. A process according to claim 1, wherein the gaseous mixture to be fractionated contains an acid gas and a hydrocaroon.

6. A process according to claim 5, wherein the acid gas proportion of the depleted sidestream fluid is at most 5 mol %.

7. A process according to claim 1, wherein a stream enriched in $CO_2$ is recovered as bottoms from said fractionating column, another stream enriched in $CO_2$ is removed from said sidestream fluid, and said two enriched streams are combined.

8. A process according to claim 7, wherein said separating of said fluid is conducted by diffusion on semipermeable membranes.

9. A process according to claim 7, wherein the gaseous mixture to be fractionated is a gas recycled from tertiary oil recovery.

10. A process according to claim 1, wherein the gaseous mixture to be fractionated is a $CO_2$-containing motive gas recycled from tertiary oil recovery wherein a gas enriched in $CO_2$ is recovered from the bottom of said fractionating column and further comprising employing said $CO_2$-enriched gas as motive gas in said tertiary oil recovery.

11. A process according to claim 10, wherein said separating of said fluid is conducted by diffusion on semipermeable membranes.

12. A process according to claim 1, wherein said gaseous mixture to be fractionated consists essentially of methane, carbon dioxide and ethane, the latter being the component having the highest dissolving capacity for carbon dioxide.

13. A process according to claim 12, wherein the fluid withdrawn from the column during fractionation is separated to remove carbon dioxide and to obtain an ethane-enriched liquid, said liquid being recycled to the fractionating column.

14. A process according to claim 13, wherein the ethane-enriched fluid is recycled into the column above the point of withdrawal.

15. A process according to claim 14, wherein the withdrawn fluid is separated by semi-permeable membranes to remove both carbon dioxide and methane selectively from the fluid, thereby obtaining an enriched stream of ethane which is recycled into the column.

16. A process according to claim 14, wherein the gaseous mixture to be fractionated consists essentially by volume of about 5–20% methane, about 50–90% carbon dioxide and about 2–10% ethane.

17. A process according to claim 1, wherein the component which is removed from the sidestream is also the main component which is gathered is gathered in the sump of the frationating column.

18. A process according to claim 1, wherein the gaseous mixture contains $CO_2$, said $CO_2$ being the component which is removed from the sidestream.

* * * * *